United States Patent
Korzeniowska-Kowal et al.

(10) Patent No.: US 9,938,338 B2
(45) Date of Patent: Apr. 10, 2018

(54) ANTIBODY POSSESSING AN AFFINITY FOR EPITHELIAL SECRETORY AND NERVOUS TISSUE, AS WELL AS TUMOUR TISSUE DERIVED FROM THESE TISSUES AS WELL AS THE USE THEREOF

(71) Applicants: INSTYTUT IMMUNOLOGII I TERAPII DOSWIADCZALNEJ PAN, Wroclaw (PL); UNIWERSYTET MEDYCZNY IM. PIASTOW SLASKICH WE WROCLAWIU, Wroclaw (PL)

(72) Inventors: Agnieszka Korzeniowska-Kowal, Miekinia (PL); Agata Kochman, Glasgow (GB); Piotr Ziolkowski, Wroclaw (PL); Andrzej Gamian, Wroclaw (PL)

(73) Assignees: INSTYTUT IMMUNOLOGII I TERAPII DOSWIADCZALNEJ PAN, Wroclaw (PL); UNIWERSYTET MEDYCZNY IM. PIASTOW SLASKICH WE WROCLAWIU, Wroclaw (PL)

( * ) Notice: Subject to any disclaimer, the term of this patent is extended or adjusted under 35 U.S.C. 154(b) by 0 days.

(21) Appl. No.: 15/108,202

(22) PCT Filed: Dec. 29, 2014

(86) PCT No.: PCT/PL2014/050080
§ 371 (c)(1),
(2) Date: Jun. 24, 2016

(87) PCT Pub. No.: WO2015/009548
PCT Pub. Date: Jul. 2, 2015

(65) Prior Publication Data
US 2016/0326235 A1 Nov. 10, 2016

(51) Int. Cl.
C07K 16/18 (2006.01)
C07K 16/12 (2006.01)
C07K 16/30 (2006.01)
C07K 14/245 (2006.01)
G01N 33/569 (2006.01)

(52) U.S. Cl.
CPC ........ C07K 16/1232 (2013.01); C07K 14/245 (2013.01); C07K 16/18 (2013.01); C07K 16/3076 (2013.01); G01N 33/56911 (2013.01); C07K 2317/33 (2013.01); C07K 2317/34 (2013.01); C07K 2317/92 (2013.01); G01N 2400/50 (2013.01); G01N 2469/10 (2013.01)

(58) Field of Classification Search
None
See application file for complete search history.

(56) References Cited

PUBLICATIONS

Gamian et al. (FEMS Microbiology Immunology, 89:323-328, 1992).*
Gamian A et al: "Immunochemical studies onsialic acid-containing lipopolysaccharides from enterobacterial species", FEMSMicrobiology Letters, Wiley-Blackwell Publishing Ltd, GB, vol. 89, No. 6, Aug. 1, 1992 (Aug. 1, 1992), pp. 323-328.
Ida Orskov et al: "Serology, Chemistry, and Genetics of 0 and K Antigens of *Escherichia coli* Techniques for 0-Antigen Determination669 Cross-Reactions Between 0 Antigens of", Copyright, Jan. 1, 1977 (Jan. 1, 1977), pp. 667-710.
Andrzej Gamianl et al: "Analysis of 7-Substituted Sialic Acid in Some Enterobacterial Lipopolysaccharides", Journal of Bacteriology, Mar. 1, 1993 (Mar. 1, 1993), pp. 1508-1513.
Gabriela Bugla-Ploskonska et al: Bactericidal activity of normal bovine serum (NBS) directed against some Enterobacteriaceae with sialic acid-containing lipopolysacchairides (LPS) asa component of cell wall, Polish Journal of Microbiology, vol. 55, No. 3, Jan. 1, 2006 (Jan. 1, 2006), pp. 169-174.
Lu et al: "Generation and characterization of hybridoma antibodies for immunotherapy of tularemia", Immonology Letters, Elsevier BV, NL, vol. 112, No. 2, Sep. 14, 2007 (Sep. 14, 2007), pp. 92-103.
Andrzej Gamian et al: "Structure of the *Escherichia coli* 024 and 0 5 6 0-specific sialic-acid-containing polysaccharides and linkage of these structures to the core region in lipopolysaccharides", European Journal of Biochemistry, vol. 225, No. 3, Nov. 1, 1994 (Nov. 1, 1994), pp. 1211-1220.
Ordonez Nelson G: "Broad-spectrum immunohistochemical epithelial markers: a review", Human Pathology, Saunders, Philadelphia, PA, US, vol. 44, No. 7, Feb. 18, 2013 (Feb. 18, 2013), pp. 1195-1215.
Jiansong Cheng et al: "Characterization of *E. coli* 024 and 056 0 Antigen Gene Clusters Reveals a Complex Evolutionary History of the 024 Gene Cluster", Current Microbiology, Springer-Verlag, NE, vol. 53, No. 6, Oct. 26, 2006 (Oct. 26, 2006), pp. 470-476.

* cited by examiner

*Primary Examiner* — Brian Gangle
(74) *Attorney, Agent, or Firm* — Arrigo, Lee, Guttman & Mouta-Bellum LLP

(57) ABSTRACT

We disclose the use of bacterial antigens and obtained antibodies. The resulting antibodies can be used in the diagnosis of tumors by immunohistochemistry and in the binding of drugs to antibodies for use in cancer therapy.

6 Claims, 9 Drawing Sheets

Figure 1:
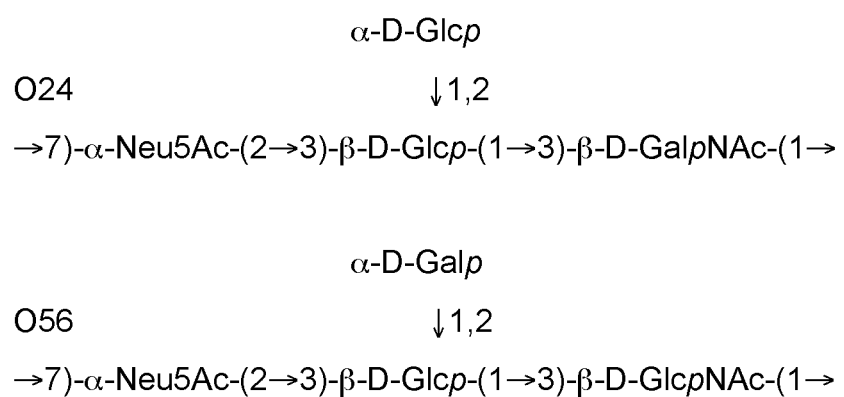

ANTIBODY POSSESSING AN AFFINITY FOR EPITHELIAL SECRETORY AND NERVOUS TISSUE, AS WELL AS TUMOUR TISSUE DERIVED FROM THESE TISSUES AS WELL AS THE USE THEREOF

The present invention relates to a new use of bacterial antigens and antibodies obtained in accordance with this use. The resulting antibodies can be used in the diagnosis of tumours by immunohistochemistry and in the binding of drugs to antibodies for application in cancer therapy.

Lipopolysaccharide (LPS) is an endotoxin molecule located on the cell surface of Gram-negative bacteria. It consists of a toxic component, lipid A, a core region, and an O-polysaccharide antigen which is specific for each serotype [1]. O24 and O56 serotypes of Escherichia coli are characterized by the presence of sialic acid in their lipopolisacharydach. The presence of sialic acid in LPS contributes to the pathogenicity of bacteria by a mechanism of molecular mimicry, ie. sharing a common epitope with host structures [2]. The presence of bacterial epitopes structurally similar to host antigens, the molecular mimicry phenomenon, may interrupt the host immune response. O-specific polysaccharides of E. coli O24 and O56 have a similar sequence of sugars with a common structure →7)-α-NeuNAc-(2→3)-β-D-Glc(1→. Sialic acid is glycosylated by β-D-GlcpNAc in O56 and β-D-GalpNAc in O24 polysaccharides respectively [3]. The molecular mimicry based on the presence of sialic acid epitopes in common with the host structures may be supported by a well-known example of a bacterial colominic acid being structurally identical to a tissue polisialyl-glycoconjugate [4], or to O-specific polysaccharide O37 of Citrobacter cross-reactive with the band 3 glycoprotein of human erythrocytes [5]. Of particularly importance is the expression of sialic acid on the surface of tumor cells, indicating a functional relationship with the neoplasmic phenotype. The transformation progression and metastasis accompanied by changes in the amounts, connectivity and types of sialic acids on the surface of tumor cells [6].

The specific recognition of particular cancers is still a problem in need of a solution. It is particularly desirable to provide a new diagnostic tool for the identification and differentiation of secretory epithelial cancers and nervous tissue.

Unexpectedly, it turned out that the above defined problem has been solved in the present invention.

The subject of the present invention is an antibody having an affinity for secretory epithelial and nervous tissue and tumour tissue derived from these tissues recognizing a bacterial antigen comprising a structural motif defined by the formula:

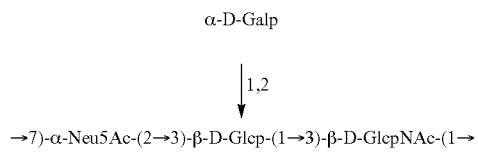

Another object of the invention is a diagnostic kit for the detection of secretory epithelial cells and neural tissue and tumour tissue cells derived from these tissues, comprising an antibody as defined above.

Another subject of the present invention is the use of the antigen defined by the formula above in the production of antibodies specific for secretory epithelial and nervous tissue and tumour tissue derived from these tissues.

Preferably, the antibodies are produced for the diagnosis of tumours.

Another subject of the present invention is a method for the preparation of antibodies specific for secretory epithelial and nervous tissue, characterized in that the mammal is immunized with a bacterial antigen defined by the formula above, then antibodies that recognize the antigen are isolated.

Preferably, the antibodies are isolated using affinity chromatography on a column packed with a carrier containing the immobilized antigen defined by the formula above.

Unexpectedly, as a result of the research forming the basis for the present invention, it turned out that selected human tissues are recognized specifically by anti-A24 or anti-O56, although some of the epitopes were recognized by both anti-A24 and anti-O56. Furthermore, preferential reactivity with anti-O56 was found. Many tissues tested did not react with any of the two antibodies, confirming the specificity of the observed phenomenon.

Immunohistochemistry experiments demonstrated that antibodies against the O-specific polysaccharide of Escherichia coli O24 and O56 recognize different epitopes on human tissues. An unexpected fact is the recognition of tissue structures by rabbit antibodies obtained after immunization with bacterial cells of Escherichia coli O24 and O56, purification affinity chromatography on a column of immobilized lipopolysaccharide. Unexpectedly, we noted the high reactivity of these antibacterial antibodies with tumour tissue, especially cancer tissue, and particular specificity for secretory epithelial and neural tissue. Particularly interesting is the discovered reactivity of anti-O24 and O56 anti-tumour reactivity with several structures that can be used in the diagnosis of cancer and oncology.

To facilitate a better understanding of the present invention, the above description has been enriched with the accompanying figures and discussion of example embodiments of the present invention.

LIST OF FIGURES

FIG. 1. The structure of O-specific polysaccharide from E. coli O24 and O56.

Figure 2:
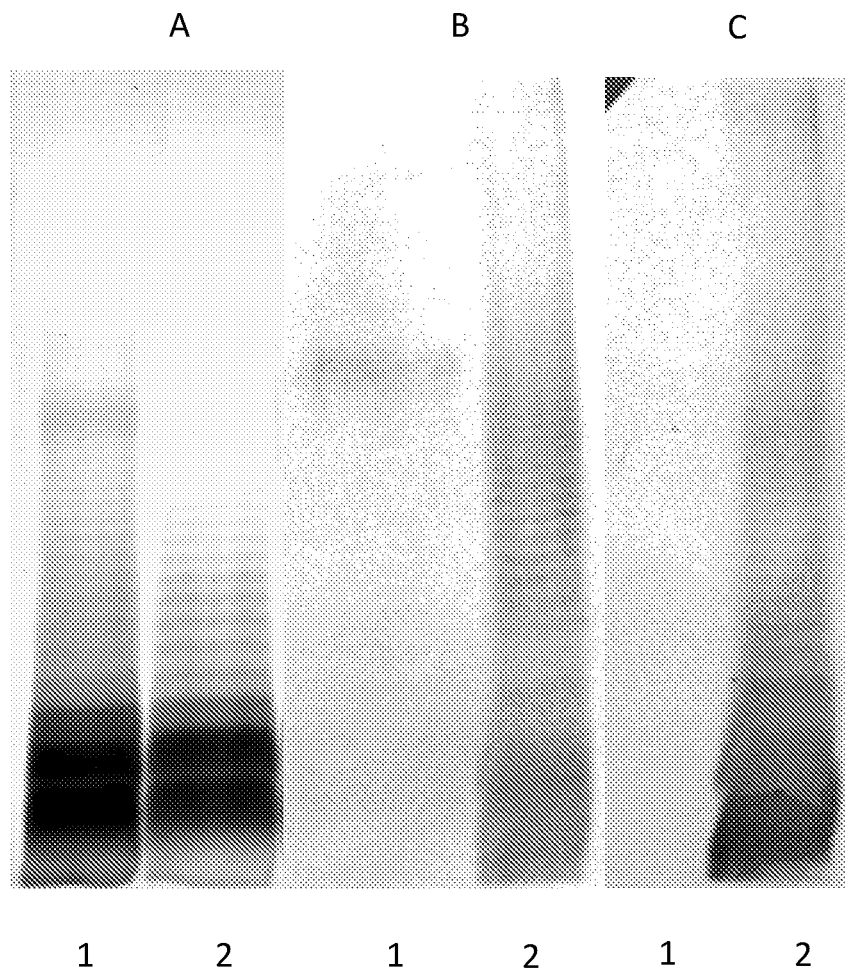

FIG. 2. SDS-PAGE analysis of lipopolysaccharide from E. coli serotype O24 (1) and O56 (2) (A) and immunoblotting with rabbit antibodies using affinity-purified anti-E. coli O24 (B) and anti-E. coli O56 (C).

Figure 3:
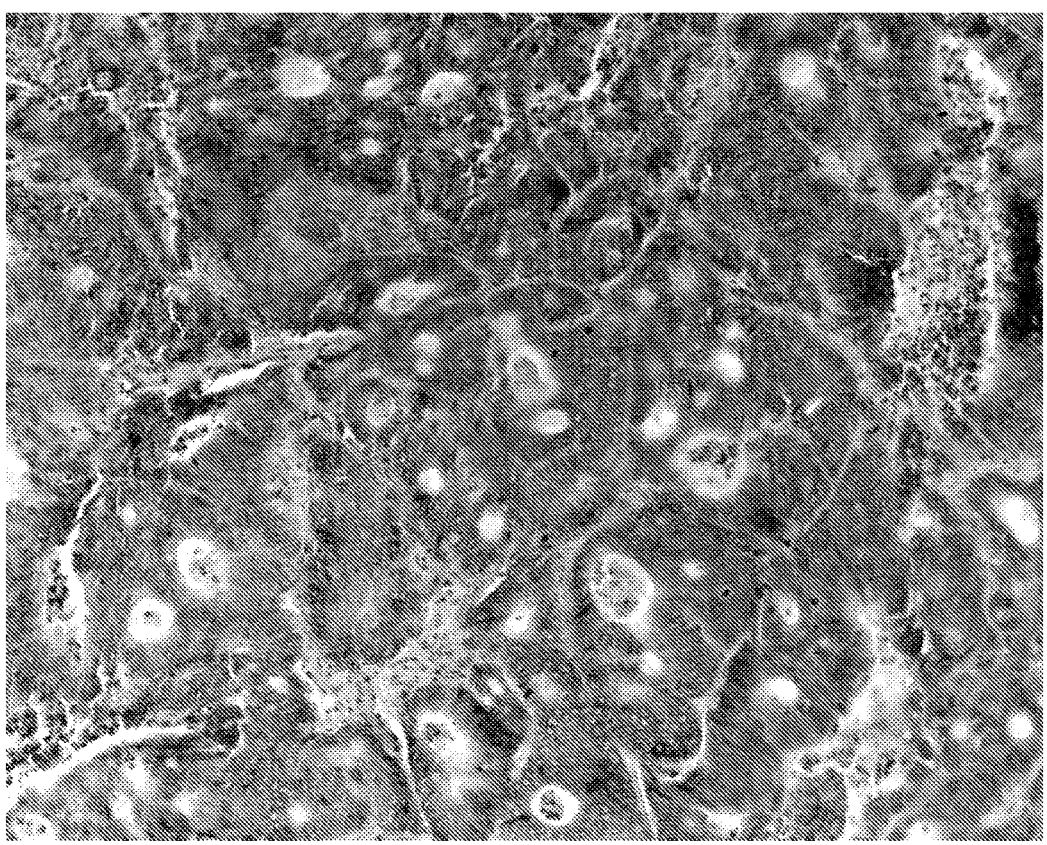

FIG. 3. Metastatic adenocarcinoma of the colon in the liver. Strong positive staining is seen in the secretory cells of the metastasis with anti-O56; LSAB, counterstained with hematoxylin, 100× magnification.

Figure 4:
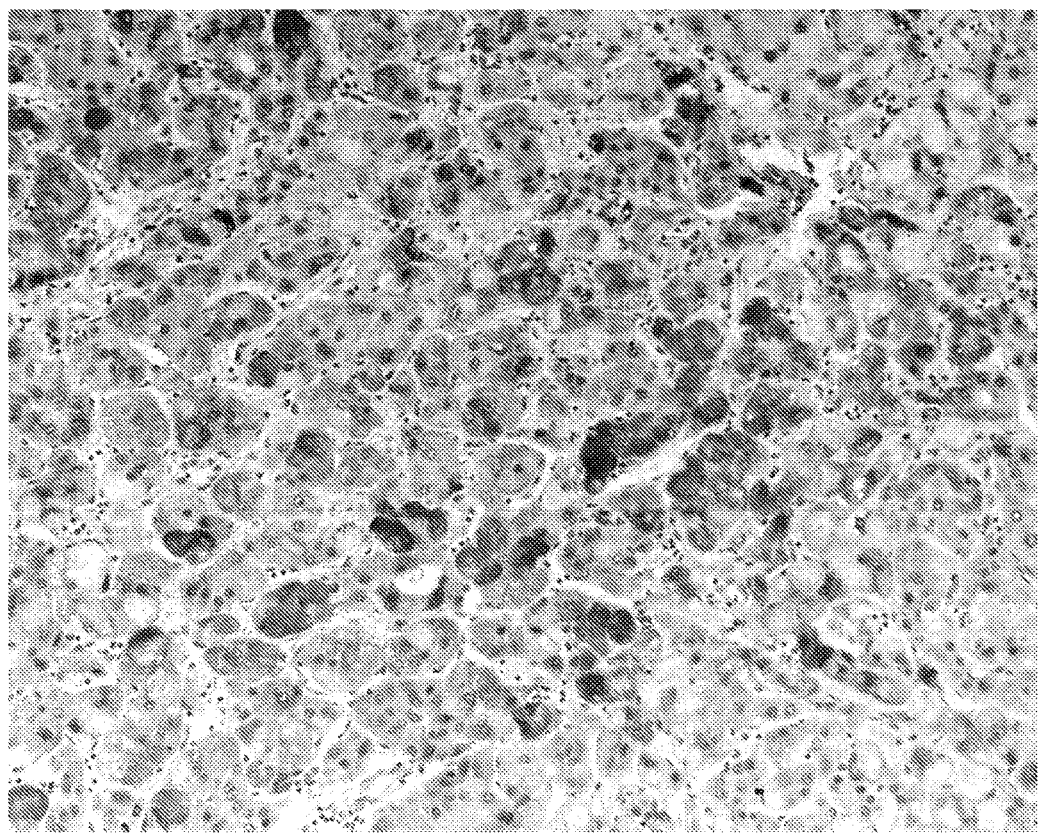

FIG. 4. Hepatocellular carcinoma (HCC). HCC cells reveal a strong reaction with the anti-dispersed O56; LSAB, counterstained with hematoxylin, 100× magnification.

Figure 5:
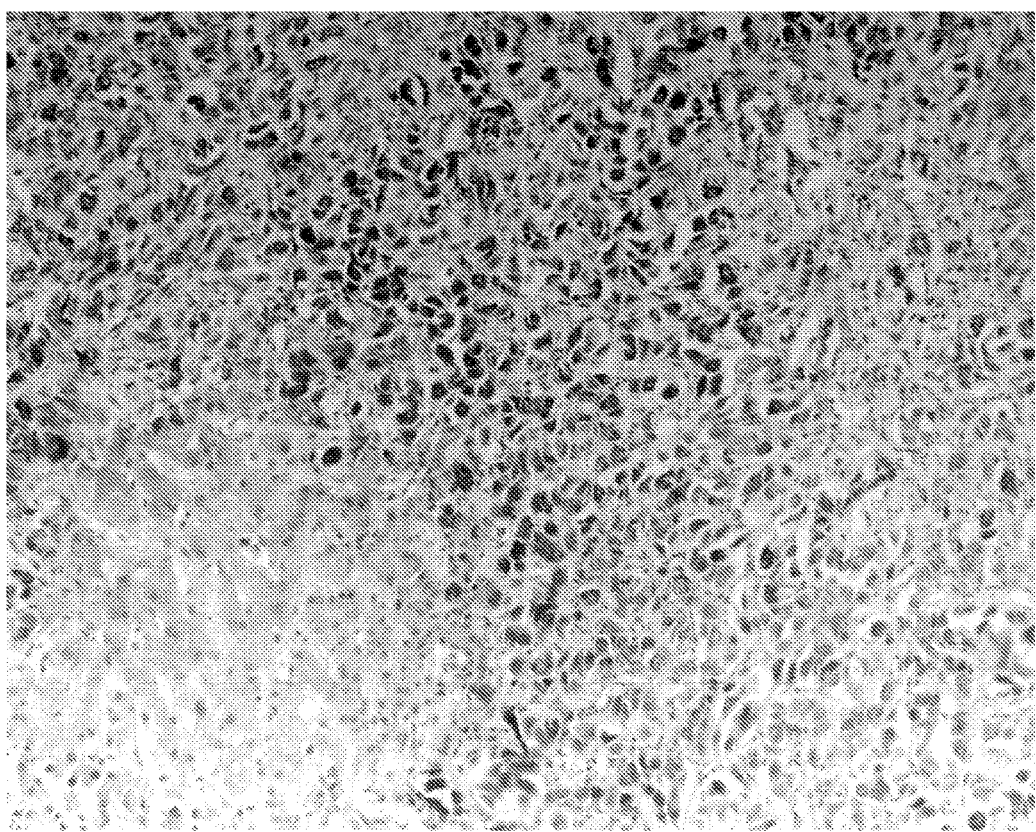

FIG. 5. Cancer of bile duct cells (CCC). CCC cells reveal a very strong dispersed reaction with anti-O56 antibodies; LSAB, counterstained with hematoxylin, 100× magnification.

Figure 6:
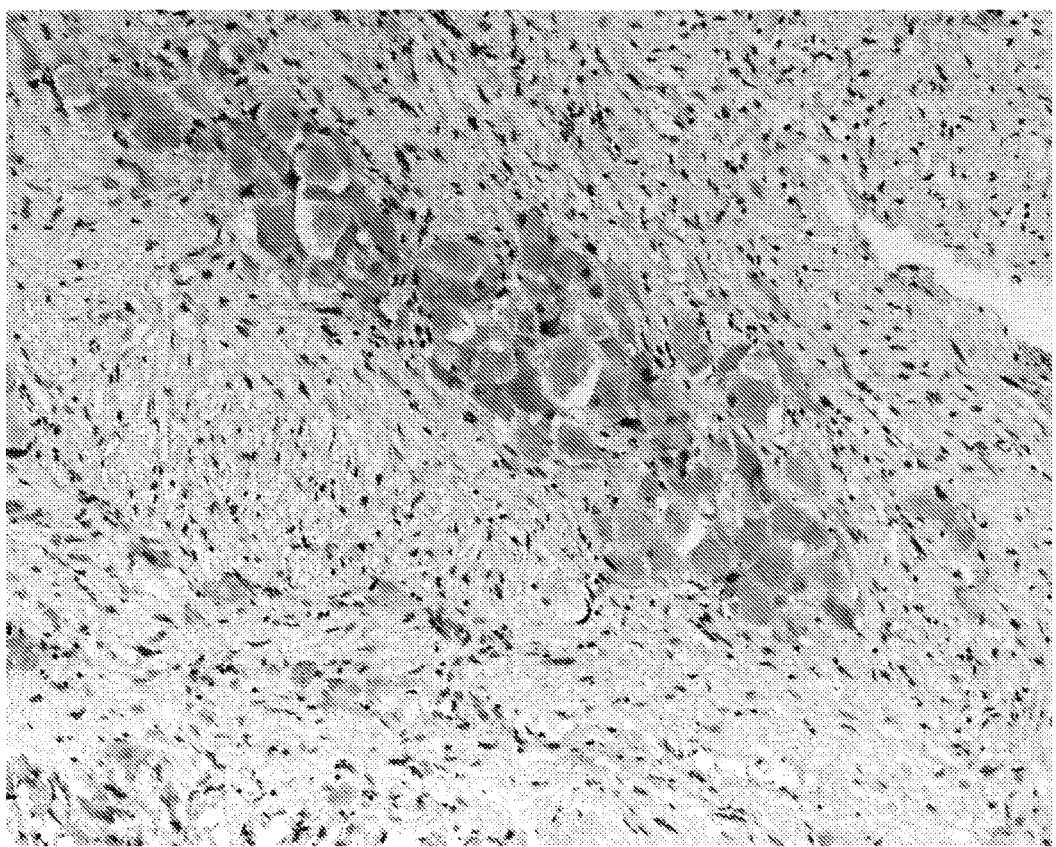

FIG. 6. Coil neuroma. Visible in the center of the photomicrograph is a moderate positive response of ganglion cells of the benign tumour with anti-O56; LSAB, counterstained with hematoxylin, 100× magnification.

Figure 7:
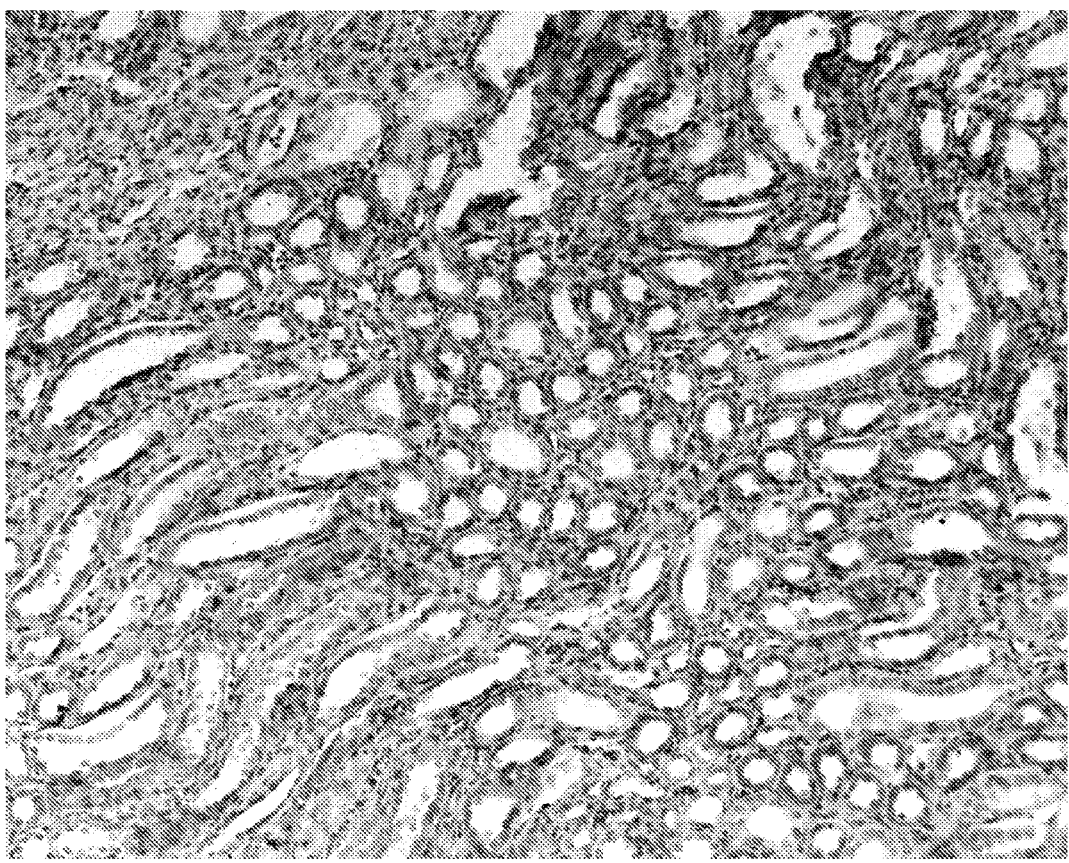

FIG. 7. Chronic kidney transplant rejection. Renal tubular cells show strong positive staining with anti-O56; LSAB, counterstained with hematoxylin, 100× magnification.

Figure 8:
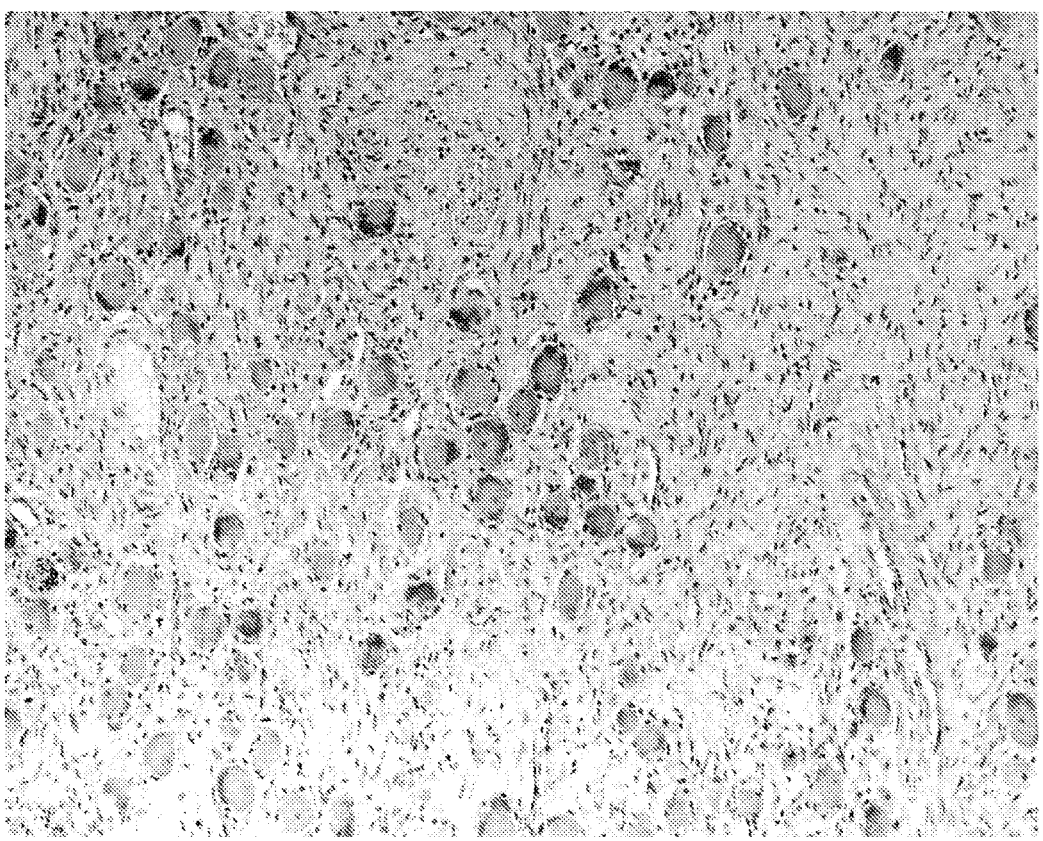

FIG. 8. Neural coils. Ganglion cells show a moderate positive reaction with anti-O56; LSAB, counterstained with hematoxylin, 100× magnification.

Figure 9:
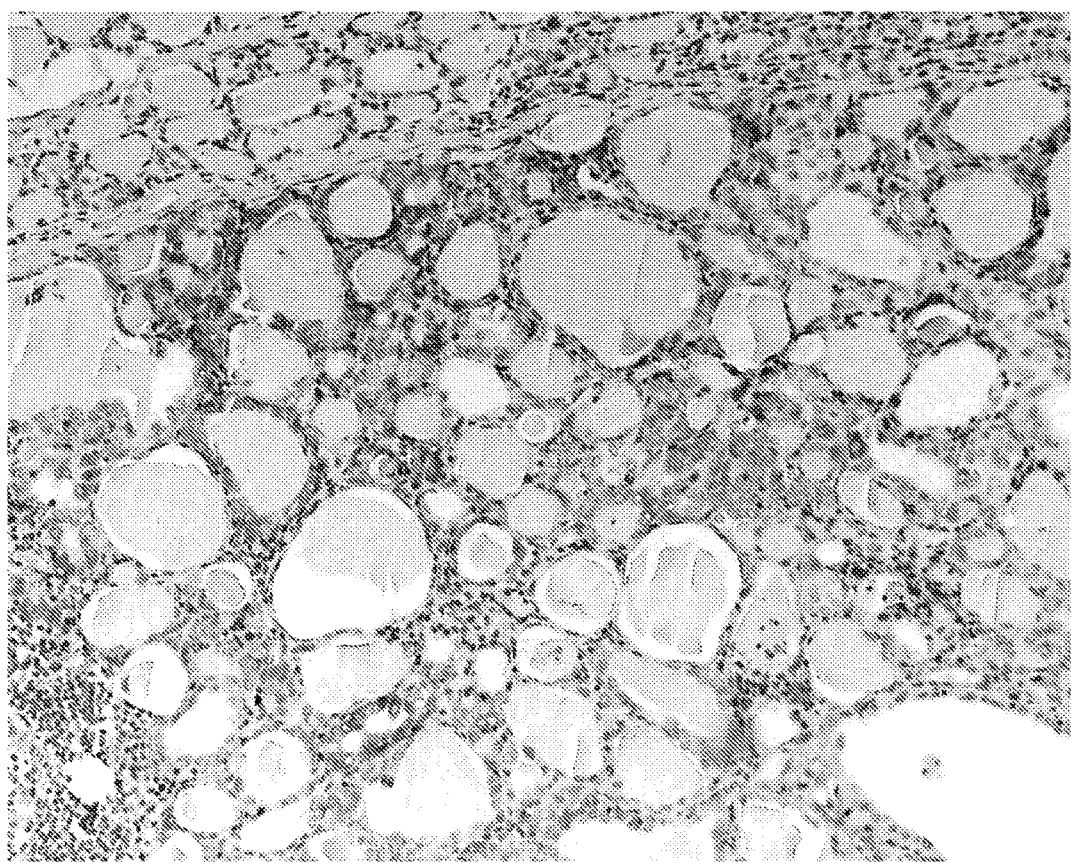

FIG. 9. The thyroid gland. Thyrocytes (thyroid epithelial cells) in normal thyroid show a strong reaction with the anti-O56 antibody; LSAB, counterstained with hematoxylin, 100× magnification.

EXAMPLE 1

Preparation of the Antibodies of the Present Invention

Bacterial Strains and Culture Conditions.

Bacterial strains were obtained from the Polish Collection of Microorganisms (PCM) at the Institute of Immunology and Experimental Therapy, Polish Academy of Sciences in Wroclaw. *Escherichia coli* O24 (PCM 195), and O56 (PCM 2372) were the same as used previously [3]. The bacteria were grown in nutrient Davis broth, supplemented with casein hydrolyzate and yeast extract (Difco), with aeration at 37° C. After 24 h, the cells were collected and lyophilized. Lipopolysaccharides were obtained by extraction using phenol-water and purified by ultracentrifugation [7].

Isolation and analysis of LPS, using the proteinase K method.

An original procedure [8] was slightly modified as follows. The bacterial suspension in phosphate buffered saline (PBS) adjusted to a concentration with a uniform optical density of A600=0.3, then 1.5 ml of this material was centrifuged (13 000 g, 4° C., 15 min). Pelleted cells were resuspended in 200 ul of 10 mM Tris-HCl buffer containing EDTA, glycerol and SDS, boiled for 10 minutes and treated with proteinase K at 60° C. for 2 hours. After removal of the precipitate, the solution was subjected to polyacrylamide gel electrophoresis in the presence of SDS, followed by an immunoblotting assay.

Serum Preparation

Rabbits were immunized with lyophilized bacteria suspended in PBS, initially subcutaneously at a dose of 100 mg of dry cells per 1 ml in PBS and then IV twice a week with increasing amounts of bacteria (100 to 6400 mg/ml PBS). One week after the last immunization the rabbits were bled and the serum was separated and the complement was heat inactivated (56° C., 30 min) and stored at −20° C. [9].

Purification of Antibodies by Affinity Chromatography Using Bound Lipopolysaccharides.

The soluble form of lipopolysaccharide of *E. coli* O24 and O56 (20 mg) was obtained by suspending it in 2 ml of 2% SOS in 200 ml of 0.5 M EDTA and then three times by ethanol precipitation (1:4, v/v) and centrifugation (12,000 rpm per minute for 20 minutes). LPS was dissolved in water (1 mL), sonicated and passed through a column of DOWEX ion exchange resin H+ or DOWEX ion exchange resin Na+ to obtain preparations, respectively of acid or sodium salts. The antibodies were isolated from rabbit sera against *E. coli* O24 and O56 (20 ml) diluted in PBS (1:2, v/v) after salting out with ammonium sulfate (9.6 g (NH4) 2SO4), 4° C., 1 h, 30 min centrifugation of 3000×g, 25° C.). The precipitated antibodies were dissolved in 5 ml of PBS and dialyzed to PBS at 4° C. The affinity column was prepared by binding the acid form of LPS to C18 silica gel in DMSO, after washing out the unbound LPS with 50% methanol, this was packed into a column (1×10 cm) in 50% methanol, washed with water and PBS, then blocked with 1% casein in PBS, and washed with PBS with monitoring at 280 nm. The salted out antibodies (0.5 ml) were bound to the affinity column with LPS-bound C18 silica gel, washed with PBS to remove unbound protein and the antibody was eluted with 3 M KSCN in PBS, dialyzed against PBS and then stored in 50% glycerol at −20° C.

EXAMPLE 2

The Use of Antibodies According to the Present Invention

SDS-PAGE and Immunoblotting

SDS-PAGE was performed by the Laemmli [10] method using a 15% polyacrylamide gel as previously described [3]. In short, resuspended LPS (1 mg/ml) in sample buffer or samples treated with proteinase K, and bacterial extract was boiled for 5 minutes and 10 ml were loaded onto the gel. After electrophoresis, the gels were stained with silver according to Tsai and Frash [11,12]. After SDS-PAGE, immunoblotting test material was transferred electrophoretically from the gel to a nitrocellulose membrane (Schleicher-Schuell, 0.45 um) as described previously [13]. The membranes were incubated overnight at 36° C. in a rabbit serum diluted 1:200 with 1% (w/v) gelatin, washed with Tris-buffered saline (TBS, 20 mM Tris-HCl, 50 mM NaCl, 0.05% TWEEN polysorbate 20, pH 7.5) and then incubated with goat anti-rabbit IgG conjugated with horseradish peroxidase diluted 1:5000 in TBS containing 1% (w/v) gelatin for 1 hour at 36° C. The membrane was stained with 4-chloro-1-naphthol in the presence of $H_2O_2$.

Immunohistochemical Staining

Human tissue sections, fixed in formalin (4%) and paraffin-embedded (FFPE), were cut from blocks 4 μm slices and deparaffinized. The procedure using an immunoperoxidase ABC kit from DAKO: endogenous peroxidase was blocked with blocking reagent and distilled water at room temperature (15 min); then acid citrate buffer pH 6.0 (2×8 min for the first time in the microwave at a power of 350 W, and then at room temperature), TBS (0.05 mmol, pH 7.6) with swine serum 1:50 (0, 5 hours at room temperature), distilled water, the test antibody (150 ul/formulation, 40° C., overnight) TBS; LSAB reagent (30 min), 3,3'-diaminobenzidine tetrahydrochloride (DAB) (5 min). Sections were stained with hematoxylin and embedded in the resin layer. Negative controls were performed in TBS, and without the primary antibody.

Results

Bacterial cells of the O24 and O56 serotypes of *E. coli* were grown in liquid medium for obtaining and analyzing the lipopolysaccharide. LPS preparations were isolated from the cell mass by extraction with phenol-water at a preparative scale. The method of isolation of LPS with proteinase K is used in quantiative analysis. The structures of sialic acid-containing polysaccharides have been established previously [3], are shown in FIG. 1. The purified LPS were bound to a solid phase and an affinity column prepared from the acidic form of LPS and C18 silica gel. Rabbit polyclonal antisera were prepared against whole bacterial cells. For the purification of antibodies using affinity, immunoglobulin fractions were precipitated with ammonium sulfate. The antibodies of this fraction were specifically bound to immobilised LPS and eluted with KSCN. The obtained antibody was then subjected to SDS-PAGE followed by an immunoblotting analysis. As shown in FIG. 2, the resulting antibodies recognize the corresponding lipopolysaccharides. It should be noted that, in particular, antibodies against *E. coli* O24 showed cross-reactivity with the LPS of *E. coli* O56, while the anti-O56 antibodies should be viewed as only reactive with the homologous LPS. This mild method of binding LPS is particularly valuable in the case of labile compounds, such as sialic acid-containing polysaccharides. Anti-*E. coli* O56 recognize long chains of LPS molecules present in small quantities, which have been difficult to visualize using silver staining. Structural differences between the O-specific units are responsible for the lack of serological cross-reactivity with *E. coli* O56, but have a similar sugar backbone. Rabbit antibodies obtained by purification using the affinity reaction were investigated through immunohistochemistry with selected strips of human tissues. For these experiments we used normal healthy tissues, as well as rejected kidney preparations, derived from the original benign and malignant tumours, and metastatic cancer. The results are shown in FIG. 3-9. No staining for either antibody (O24 and O56) has been demonstrated in:

1. The following normal tissues and cells: parathyroid glands, adrenal glands, lymphatic vessels or blood vessels, bronchial squamous epithelium, ovarian serous epithelium, bone, T and B cells, macrophages, granulocytes and nerve cells,
2. Benign tumours: lipomas and papillomas,
3. Cancers, such as the gastrointestinal stromal tumour (GIST), cancer, nasopharyngeal cancer, and small cell bronchial squamous cell, basal cell carcinoma, malignant melanoma and fatty sarcoma.

We noticed an intense positive antibody response of *E. coli* O56 antibody in bronchial adenocarcinoma cells (adenocarcinoma), and liver cancer metastases with moderately differentiated adenocarcinoma of the colon, where the glands are less regular (FIG. 3). A similar reaction with the antibody was found in adenocarcinoma of the pancreas and slightly weaker endometrial cancer (data not shown). These antibodies react with an as yet uncharacterised antigen present on hepatocytes, as shown in FIG. 4. Based on the granular nature of the intracellular staining, it can be assumed that the epitope may be located in the cytoplasm [14]. Immunohistochemistry plays an important role in distinguishing hepatocellular carcinoma (HCC) from the other primary and metastatic tumours. It is known that no more specific nor sensitive marker for HCC has yet been established. In this case, it is recommended to use an immunohistochemical library including a plurality of antibodies, such as those specific for an antigen hepatocyte PCEA, MOC-31, CD34, TTF-1 [15]. Based on this information, an *E. coli* O56 antibody can be suggested as useful in combination with other known markers, and not used as a sole marker. A positive antibody reaction to either *E. coli* O56 and O24 of *E. coli* antibodies is found in many juvenile malignant tumours, for example. Hepatoblastoma, germ gliomas or meningioma, which is usually in a mild form and with a very strong reaction observed for cancers of the bile duct (FIG. 5). Interestingly, a benign tumour, the neuroganglioma demonstrates that the tissues of neuroectodermal origin are recognized by antibodies *E. coli* O56 (FIG. 6) and only trace resactivity was found with *E. coli* O24. Normal renal tubule cells (FIG. 7), ganglion cells (FIG. 8), and normal thyroid epithelial cells of the thyroid gland (FIG. 9) were stained with both antibodies and demonstrated a much stronger reaction with the antibody against *E. coli* O56. During the tests using neuroectodermal tissues (ganglions, nerves and brain), we demonstrated the reactivity of our antibody in normal tissues (ganglia) as well as in tumour tissue (neuroganglioma). Digestive glands, derived from the endoderm and the thyroid gland also showed a positive reaction with the antibody of *E. coli* O56. An interesting observation is that the normal thymus, spleen and tonsils do not show immunoreactivity, indicating that the results are significant.

Generally, the antibodies against *E. coli* O56 are more reactive in staining of nervous tissue and epithelial cells than antibodies against *E. coli* O24. The nervous system is colored in normal tissues (ganglia), and in the case of tumours (neuroganglioma). With respect to the epithelium, each type of this tissue has a different biological function, and many specific biomarker proteins. Functional markers that are generally expressed by epithelial neoplasms are useful for the immunohistochemical differentiation of metastatic tumours of unknown origin. The results of our experiments indicate that the cancers of secretory tissues, metastases, the epithelium of the renal tubules and the thyroid gland epithelium was stained, but the skin epithelium was definitely not stained (results not shown). Based on these findings, we believe that the *E. coli* O56 antibodies should be considered rather as a biomarker of secretory epithelium. Therefore, the most important observation is that the epitope recognized by anti-O56 antibodies is a new marker, specific for secretory epithelial and nervous tissue.

LITERATURE

1. Brade H., Opal S. M., Vogel S. N. & Morrison D. C. (eds) Endotoxin in Health and Disease. Macel Dekker, Inc., New York 1999
2. Corfield A. P., Schauer R. 1982: Occurrence of sialic acids, In: Sialic acids, chemistry, metabolism and function. Ed.: Schauer R. Cell Biol. Monogr. 10: 5-50.
3. Gamian A., Kenne L., Mieszala M., Ulrich J., Defaye J. 1994: Structure of the *Escherichia coli* O24 and O56 O-specific sialic-acid-containing polysaccharides and linkage of these structures to the core region in lipopolysaccharides. Eur. J. Biochem. 225: 1211-1220.
4. Janas et al, 1991
5. Ebaid H., Duk M., Gamian A. Antibodies against *Citrobacter braakii* O37 cells recognize the N-glycan of the band 3 glycoprotein of human erythrocyte membrane. FEMS Immunol Med Microbiol 52 (2008) 352-361.
6. Schultz M. J., Swindall A. F., Bellis S. L., Regulation of the metastatic cell phenotype by sialylated glycans. Cancer Metastasis Rev., published online, 2012
7. Westphal O., Jann K., Bacterial lipopolysaccharides: extraction with phenol water and further applications of the procedure, Methods Carbohydr. Chem., 5, 1965, 83-92
8. Hitchcock P. J., Brown T. M., Morphological heterogeneity among *Salmonella* lipopolysaccharide chemotypes in silver-stained polyacrylamide gels, J. Bacteriol., 154, 1983, 269-277.
9. Gamian A., Romanowska A., Romanowska E. 1992b: Immunochemical studies on sialic acid-containing lipopolysaccharides from Enterobacterial species. FEMS Microbiol. Immunol. 89: 323-328.
10. Laemmli U. K., Cleavage of structural proteins during the assembly of the head of bacteriophage T4. Nature (London) 227, 1970, 680-685
11. Tsai C. M., Frash C. E., A sensitive silver stain for detecting lipopolysaccharides in polyacrylamide gels. Anal. Biochem. 119, 1982, 115-119

12. Fomsgaard A., Freudenberg M. A. and Galanos C., Modification of the silver staining technique to detect lipopolysaccharide in polyacrylamide gels. J. Clin. Microbiol. 1990, 28; 2627-2631.
13. Towbin H., Staehelin T. and Gordon J., Electrophoretic transfer of proteins from polyacrylamide gels to nitrocellulose sheets: procedure and some applications. Proc. Natl. Acad. Sci. USA, 1979, 76; 4350-4354.
14. Minervini M. I., Demetris A. J., Lee R. G., et al., Utilization of hepatocyte-specific antibody in the immunocytochemical evaluation of liver tumors. Mol. Pathol., 1997, 10, 686-692
15. Ordonez N. G., Broad-spectrum immunohistochemical epithelial markers: a review. Human Pathology 2013, 44, 1195-1215

The invention claimed is:

1. A method comprising:
   a) providing a tissue sample;
   b) contacting the tissue sample with an antibody that binds specifically with a bacterial antigen comprising a structural motif defined by the formula:

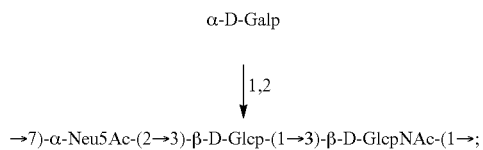

→7)-α-Neu5Ac-(2→3)-β-D-Glcp-(1→3)-β-D-GlcpNAc-(1→;

wherein the isolated antibody has an affinity for at least one of glandular epithelial cells, nervous tissue, tumour tissue derived from glandular epithelial cells, and tumour tissue derived from nervous tissue; and measuring binding of the antibody with the tissue sample.

2. The method of claim 1, wherein binding of the antibody with the tissue sample is detected.

3. The method of claim 1, wherein binding of the antibody with the tissue sample is not detected.

4. A method comprising:
   a) providing a tissue sample;
   b) contacting the tissue sample with an antibody that binds specifically with a bacterial antigen comprising a structural motif defined by the formula:

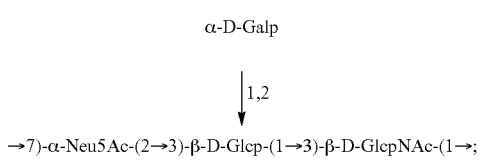

→7)-α-Neu5Ac-(2→3)-β-D-Glcp-(1→3)-β-D-GlcpNAc-(1→;

wherein the isolated antibody has an affinity for glandular epithelial cells, nervous tissue, tumour tissue derived from glandular epithelial cells, and tumour tissue derived from nervous tissue; and measuring binding of the antibody with the tissue sample.

5. The method of claim 4, wherein binding of the antibody with the tissue sample is detected.

6. The method of claim 4, wherein binding of the antibody with the tissue sample is not detected.

* * * * *

UNITED STATES PATENT AND TRADEMARK OFFICE
CERTIFICATE OF CORRECTION

PATENT NO.         : 9,938,338 B2
APPLICATION NO.    : 15/108202
DATED              : April 10, 2018
INVENTOR(S)        : Agnieszka Korzeniowska-Kowal et al.

It is certified that error appears in the above-identified patent and that said Letters Patent is hereby corrected as shown below:

On the Title Page

Item (54) at the first line of the Title:
"ANTIBODY POSSESSING AN AFFINITY FOR",
Should read:
-- AN ANTIBODY POSSESSING AN AFFINITY FOR --

Item (30) should be added and should read:
-- Foreign Application Priority Data
Dec. 29, 2014 (PL) P.406694 --

Signed and Sealed this
Seventeenth Day of July, 2018

Andrei Iancu
*Director of the United States Patent and Trademark Office*